(12) United States Patent
Abrámoff (10) Patent No.: US 8,616,702 B2
(45) Date of Patent: Dec. 31, 2013

(54) HYBRID LASER OPHTHALMOSCOPE

(75) Inventor: Michael Abrámoff, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 53 days.

(21) Appl. No.: 13/203,168

(22) PCT Filed: Feb. 25, 2010

(86) PCT No.: PCT/US2010/025369
§ 371 (c)(1),
(2), (4) Date: Nov. 10, 2011

(87) PCT Pub. No.: WO2010/099289
PCT Pub. Date: Sep. 2, 2010

(65) Prior Publication Data
US 2012/0069299 A1    Mar. 22, 2012

Related U.S. Application Data

(60) Provisional application No. 61/155,425, filed on Feb. 25, 2009.

(51) Int. Cl.
*A61B 3/14* (2006.01)
*A61B 3/10* (2006.01)
*A61B 3/00* (2006.01)

(52) U.S. Cl.
USPC ............................ 351/206; 351/205; 351/221

(58) Field of Classification Search
USPC .................................................. 351/200–246
See application file for complete search history.

(56) References Cited

U.S. PATENT DOCUMENTS

| | | | |
|---|---|---|---|
| 6,712,469 B2 * | 3/2004 | Ando | 351/211 |
| 7,232,240 B2 * | 6/2007 | Kosnik et al. | 362/259 |
| 2009/0257024 A1 * | 10/2009 | Luther et al. | 351/206 |
| 2010/0284180 A1 * | 11/2010 | Popovich et al. | 362/231 |

* cited by examiner

*Primary Examiner* — Mohammed Hasan
(74) *Attorney, Agent, or Firm* — Ballard Spahr LLP (57) ABSTRACT

Provided is a hybrid laser ophthalmoscope comprising a laser light source, a LED light source, and a holographic diffuser, wherein the holographic diffuser is configured to shape a beam of light into a Maxwellian ring.

26 Claims, 4 Drawing Sheets

HLO – optical components sketch

HYBRID LASER OPHTHALMOSCOPE

CROSS-REFERENCE TO RELATED APPLICATIONS

The present application is a National Phase Application of International Application No. PCT/US2010/025369, filed Feb. 25, 2010, which claims priority to U.S. Provisional Patent Application No. 61/155,425, filed Feb. 25, 2009, and which applications are incorporated herein fully by this reference.

GOVERNMENT SUPPORT CLAUSE

This invention was made with government support under NIH EY017066-0 awarded by the U.S. Department of Health and Human Services The government has certain rights in the invention.

SUMMARY

Provided is a hybrid laser ophthalmoscope comprising a laser light source, a LED light source, and a holographic diffuser, wherein the holographic diffuser is configured to shape a beam of light into a Maxwellian ring. Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

Figure 1:
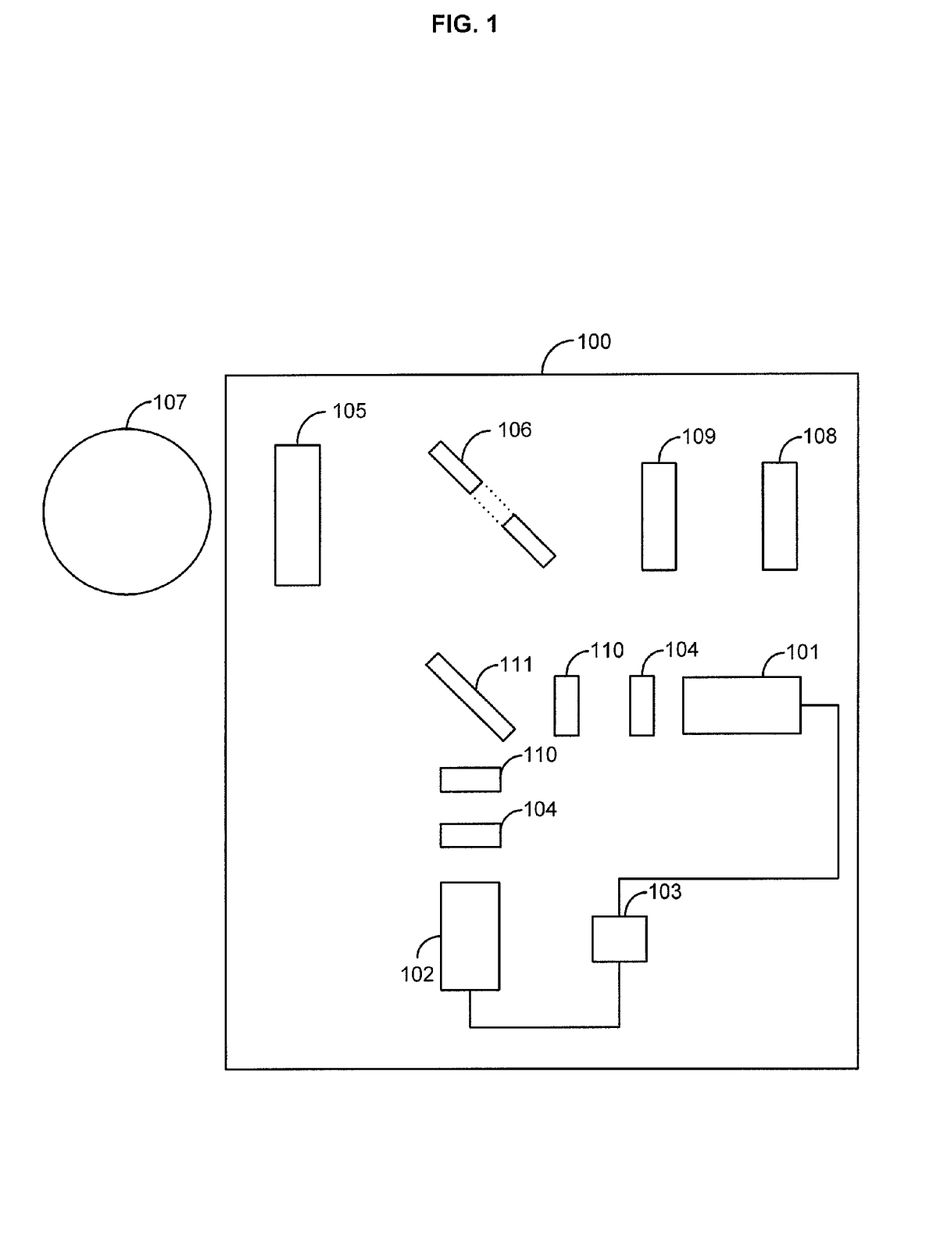
FIG. 1 is an exemplary hybrid laser ophthalmoscope.

In an aspect, illustrated in FIG. 1, provided is an apparatus 100 for examining an eye 107. The apparatus 100 can comprise a first light source 101, wherein the first light source 101 is a laser light source. The apparatus can comprise a second light source 102, wherein the second light source 102 is a Light Emitting Diode (LED) light source. A light source selection switch 103 can be coupled to the first light source 101 and the second light source 102, configured to select either the first light source 101 or the second light source 102 to illuminate an eye 107, wherein the first light source 101 or the second light source 102 becomes a selected light source upon selection. Apparatus 100 can further comprise one or more holographic diffusers 104 configured to receive light from the selected light source and to shape the light into a Maxwellian ring based on a diffraction pattern of the holographic diffuser 104. The apparatus 100 can still further comprise an imaging lens 105 coupled with one or more hole mirrors 106, wherein the imaging lens 105 and the hole mirror 106 are configured to receive the Maxwellian ring and to image the Maxwellian ring onto the eye 107. The imaging lens can be a double aspheric lens. The Maxwellian illumination system utilized in the hybrid laser ophthalmoscope uses a ring shaped illumination beam. Thus light enters the eye as far as possible from the center of the cornea (the main source of reflections) and exits the eye through center of the Maxwellian ring to be imaged in the camera.

The first light source can transmit laser light at 785 nm. The second light source can transmit red, green, or white light. The first light source can be selected for imaging blood flow and/or blood vessels having blood flow in the eye. The second light source can be selected for imaging exudates and other lesions not primarily consisting of blood, that can occur in diabetic retinopathy, hypertension, or macular degeneration.

The holographic diffuser can be generated as a digital hologram, based on a Fourier transform expanded in a Bessel function basis. The holographic diffuser can be configured to be swappable with a second holographic diffuser in order to adjust a ring diameter and local propagation direction of the light at a pupil of the eye on a per-patient basis. Because optical lenses perform a Fourier transform of the incoming light, the hologram is used to filter out part of the Fourier spectrum of the incoming light, shaping the beam. A Bessel function basis can be used to condense the Fourier spectrum into individual coefficients. Other bases can be used such as Daubechies.

The apparatus can further comprise a sensor 108, configured to receive light reflected from the imaging of the Maxwellian ring and generate an image of the eye based on the reflected light. The sensor 108 can be a complementary metal oxide semiconductor (CMOS) area sensor.

The apparatus can further comprise one or more relay lenses 109 to direct light reflected from the eye to the sensor 108. The apparatus can further comprise one or more focusing lenses 110 and dichroic mirror 111 to direct the light from first light source 101 or second light source 102 into the eye 107. One of skill in the art will appreciate that various combinations of dichroic minors and focusing lenses can be used to direct to the light to the eye.

Figure 2:
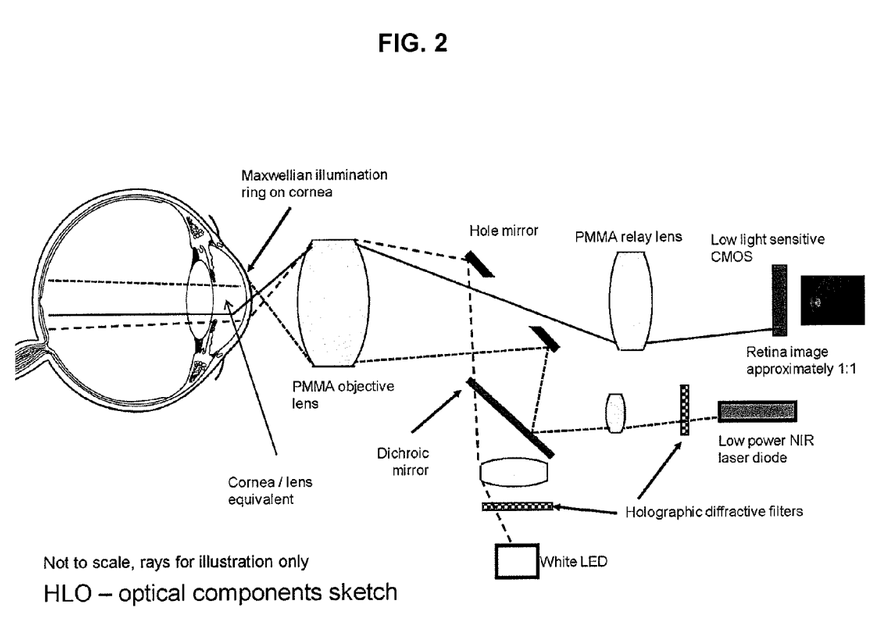
FIG. 2 is an exemplary hybrid laser ophthalmoscope.

FIG. 2 is another schematic diagram of a hybrid laser ophthalmoscope as provided herein. In an aspect, the ophthalmoscope can comprise a hybrid light source. For example, a laser light source and a LED light source. A collimated, non-confocal, laser can provide near infrared area illumination from about 850 nm to about 750 nm, for example at 785 nm, enabling "nonmydriatic" (i.e. non-pharmacologically dilated) imaging, partially increased vessel contrast, and increased vessel related abnormalities contrast. A single 4 mm focal distance achromatic beam expander can be used. A broadband visible (white, or combination of red and green) LED can be used for area illumination, enabling improved exudates contrast (white light has many wavelengths, so does not apply). An example of an LED that can be used is a Lumex SLX-LX5093. Either LED light or low power near infrared (NIR) laser light can be projected onto a retina by shaping the beam through a holographic diffractive diffuser, a focusing lens, and either passing through (LED) or reflecting off (NIR) a dichroic mirror, onto the hole minor, through the objective lens, as a ring on the cornea to minimize corneal reflections, and onto the retina. The objective lens can be a double aspheric lens.

In an aspect, the ophthalmoscope can comprise a Maxwellian illumination system using a hole minor in the illumination pathway, serving as mask, beamsplitter and imaging aperture, with focal plane in the pupil to minimize corneal reflections with a 3 mm pupil. A holographic diffuser optimized to project an isoluminant beam of either near-infrared laser light or broadband LED light onto the retina can be used. Co-axial near infrared lighting and LED visible light lighting can both be provided through the same holographic filter. The holographic diffuser can be optimized to focus a beam of light at or near the pupil plane as a Maxwellian ring, oval or other circular shape with an isoluminant profile over the ring (i.e. almost square wave illumination on the cornea). The pupil can be illuminated with the Maxwellian ring (for example, at 785 nm) that results from the diffraction pattern of the holographic diffuser. The holographic diffuser can be generated as a digital hologram, based on the Fourier transform expanded in a Bessel function basis. This can permit exploitation of the radial symmetry of the ring. The hologram can be transferred to an antireflective-coated glass plate using photolithographic techniques. The ring diameter and local propagation direction of the light at the pupil can be optimized on a per-patient basis by changing the holographic plate. This allows for minimization of corneal reflection over a range of corneal geometries with the same design. Excellent throughput is assured with the use of a spectrally narrow source and optimized antireflective coating on the holographic plate and optics. Therefore, in one aspect, co-axial near infrared and visible light illumination is provided, which does not require the use of dichroic minors or separate beamsplitters to inject both types of light into the visual axis.

In an aspect, the objective lens can comprise a double objective element fabricated using a double acrylic aspheric lens (Polymethyl methacrylate "PMMA" or similar). This forms the flat focal plane image of the retina. A specific W-coating optimized for imaging can be used with 785 nm and 565 nm light to minimize reflections. A W-coating is a coating with 2 dips (the wavelengths with minimal reflections) so can be used to protect against reflections for two different wavelengths simultaneously. The distance from an objective lens to a cornea can be from about 10 mm to about 20 mm. For example, the distance from the objective lens to the cornea can be about 15 mm.

A retinal image can be formed by the reflected light which passes through the central part of the cornea (outside the path of the illuminating light ring) through the objective lens, through the hole mirror, to form a retinal image which is then projected through a relay lens onto a CMOS sensor, resulting in a ~1:1 image of 35° of the retina.

The optics can project an illuminated area of the curved retina that has the same size as the sensor (9×6 mm) at 1:1 magnification to a flat (non-curved) sensor. Taking into account the limits of the smallest detail on the retina that can be imaged without the requirement for correction of higher order aberrations (such as adaptive optics), which is >10 µm, and the requirement for 1:1 projection, a pixel pitch of 10 µm is ample. Given the size of the sensor, a 1 Mpixel sensor can be used. A low light sensitive CMOS area (non-scanning) sensor can be used to generate an image of the retina. For example, a Micron MT9M001C12STM, Micron Tech, Boise, Id., can be used. The total optical length from cornea to sensor can be from about 10 mm to about 20 mm. For example, the total optical length can be about 110 mm.

Figure 3:
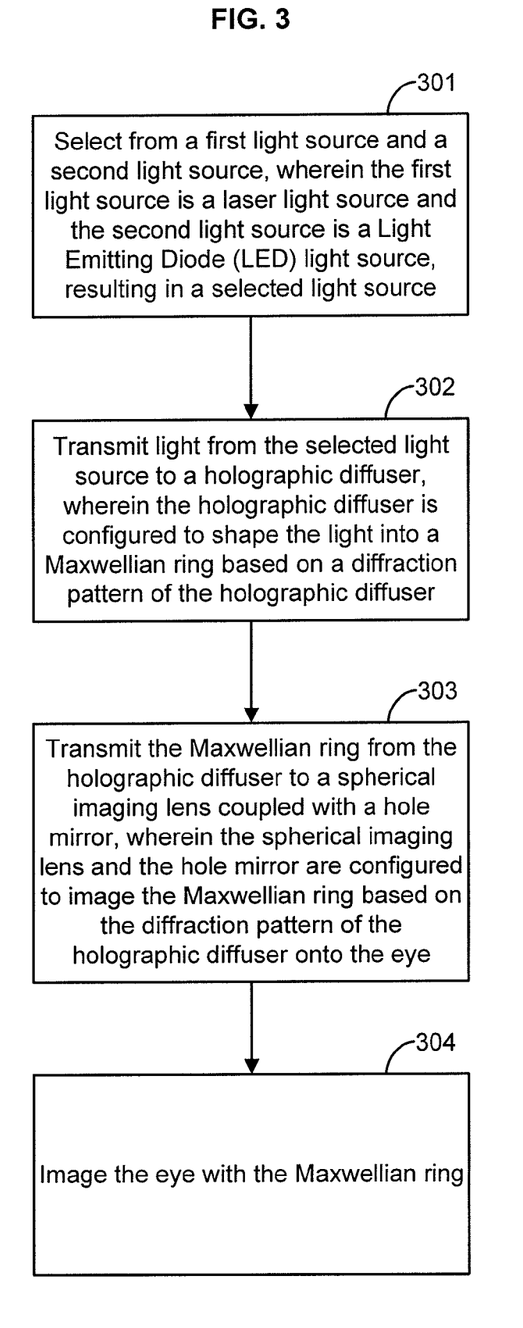
FIG. 3 is an exemplary method.

In an aspect, illustrated in FIG. 3, provided are methods for examining an eye, comprising selecting from a first light source and a second light source, wherein the first light source is a laser light source and the second light source is a Light Emitting Diode (LED) light source, resulting in a selected light source at 301, transmitting light from the selected light source to a holographic diffuser, wherein the holographic diffuser is configured to shape the light into a Maxwellian ring based on a diffraction pattern of the holographic diffuser at 302, transmitting the Maxwellian ring from the holographic diffuser to an imaging lens coupled with a hole mirror, wherein the imaging lens and the hole mirror are configured to image the Maxwellian ring based on the diffraction pattern of the holographic diffuser onto the eye at 303, and imaging the eye with the Maxwellian ring at 304. The imaging lens can be a double aspheric lens.

The first light source can transmit laser light at 785 nm. The second light source can transmits red, green, or white light. The first light source can be selected for imaging blood flow and/or blood vessels having blood flow in the eye. The second light source can be selected for imaging exudates and other lesions not primarily consisting of blood, that can occur in diabetic retinopathy, hypertension, or macular degeneration.

The methods can further comprise generating the holographic diffuser as a digital hologram, based on a Fourier transform expanded in a Bessel function basis. The methods can further comprise swapping the holographic diffuser with a second holographic diffuser in order to adjust a ring diameter and local propagation direction of the light at a pupil of the eye on a per-patient basis.

The methods can further comprise receiving light reflected from illuminating the eye with the Maxwellian ring and generating an image of the eye based on the reflected light. A complementary metal oxide semiconductor (CMOS) area sensor can receive the light reflected and generate the image.

Figure 4:
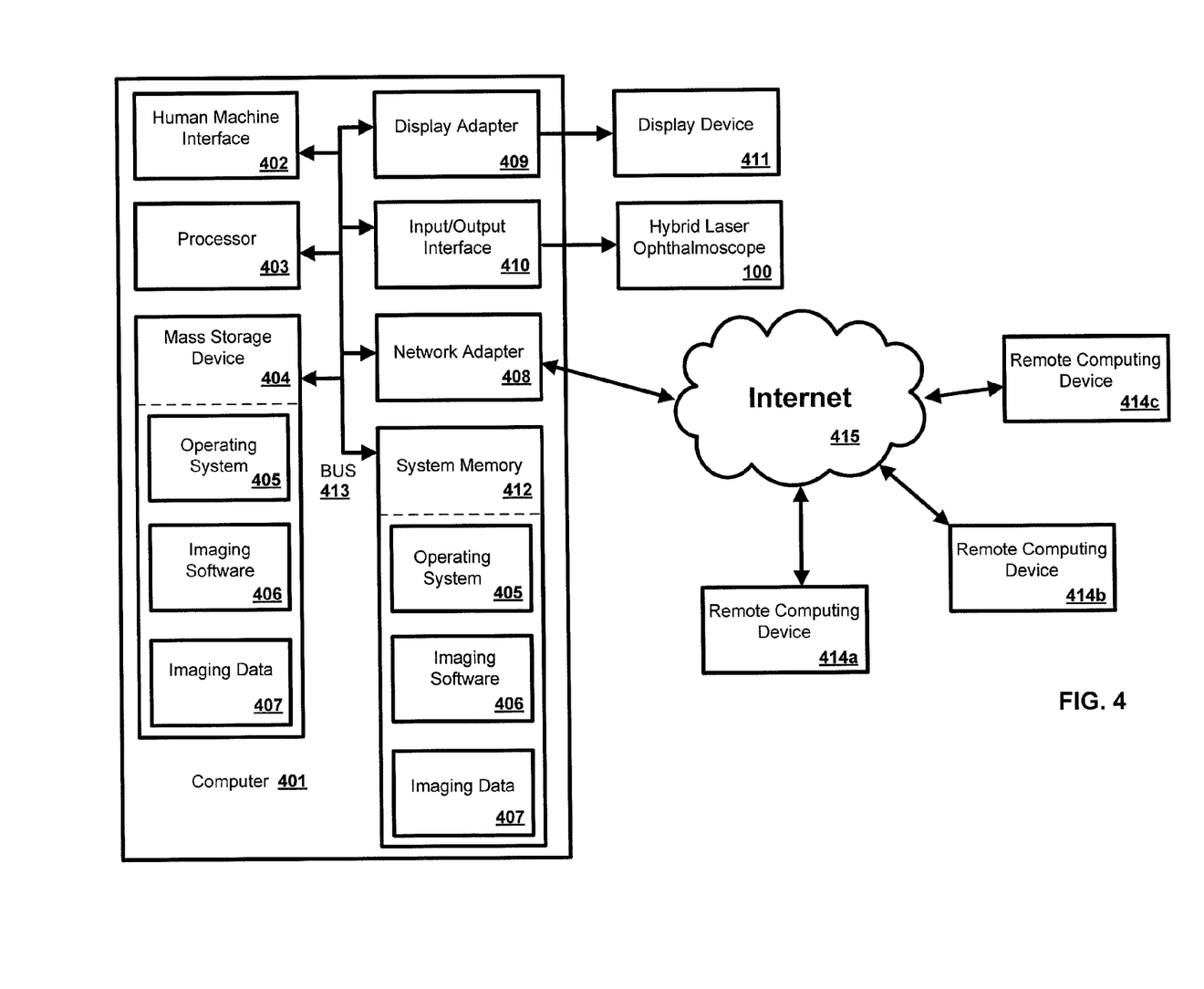
FIG. 4 is an exemplary system.

FIG. 4 is a block diagram illustrating an exemplary operating environment for performing the disclosed method. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the system and method comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed system and method can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed method can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a computing device in the form of a computer 401. The components of the computer 401 can comprise, but are not limited to, one or more processors or processing units 403, a system memory 412, and a system bus 413 that couples various system components including the processor 403 to the system memory 412. In the case of multiple processing units 403, the system can utilize parallel computing.

The system bus 413 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 413, and all buses specified in this description can also be implemented over a wired or wireless network connection and each of the subsystems, including the processor 403, a mass storage device 404, an operating system 405, imaging software 406, imaging data 407, a network adapter 408, system memory 412, an Input/Output Interface 410, a display adapter 409, a display device 411, and a human machine interface 402, can be contained within one or more remote computing devices 414a,b,c at physically separate locations, connected through buses of this form, in effect implementing a fully distributed system.

The computer 401 typically comprises a variety of computer readable media. Exemplary readable media can be any available media that is accessible by the computer 401 and comprises, for example and not meant to be limiting, both volatile and non-volatile media, removable and non-removable media. The system memory 412 comprises computer readable media in the form of volatile memory, such as random access memory (RAM), and/or non-volatile memory, such as read only memory (ROM). The system memory 412 typically contains data such as imaging data 407 and/or program modules such as operating system 405 and imaging software 406 that are immediately accessible to and/or are presently operated on by the processing unit 403.

In another aspect, the computer 401 can also comprise other removable/non-removable, volatile/non-volatile computer storage media. By way of example, FIG. 4 illustrates a mass storage device 404 which can provide non-volatile storage of computer code, computer readable instructions, data structures, program modules, and other data for the computer 401. For example and not meant to be limiting, a mass storage device 404 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 404, including by way of example, an operating system 405 and imaging software 406. Each of the operating system 405 and imaging software 406 (or some combination thereof) can comprise elements of the programming and the imaging software 406. Imaging data 407 can also be stored on the mass storage device 404. Imaging data 407 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 401 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the processing unit 403 via a human machine interface 402 that is coupled to the system bus 413, but can be connected by other interface and bus structures, such as a parallel port, game port, an IEEE 1394 Port (also known as a Firewire port), a serial port, or a universal serial bus (USB).

In yet another aspect, a display device 411 can also be connected to the system bus 413 via an interface, such as a display adapter 409. It is contemplated that the computer 401 can have more than one display adapter 409 and the computer 401 can have more than one display device 411. For example, a display device can be a monitor, an LCD (Liquid Crystal Display), or a projector. In addition to the display device 411, other output peripheral devices can comprise components such as speakers (not shown) and a printer (not shown) which can be connected to the computer 401 via Input/Output Interface 410. Any step and/or result of the methods can be output in any form to an output device. Such output can be any form of visual representation, including, but not limited to, textual, graphical, animation, audio, tactile, and the like. In an aspect, hybrid laser ophthalmoscope 100 can be coupled to computer 401 via Input/Output Interface 410. For example, hybrid laser ophthalmoscope 100 can transfer images captured to the computer 401 for analysis and storage.

The computer 401 can operate in a networked environment using logical connections to one or more remote computing devices 414a,b,c. By way of example, a remote computing device can be a personal computer, portable computer, a server, a router, a network computer, a peer device or other common network node, and so on. Logical connections between the computer 401 and a remote computing device 414a,b,c can be made via a local area network (LAN) and a general wide area network (WAN). Such network connections can be through a network adapter 408. A network adapter 408 can be implemented in both wired and wireless environments. Such networking environments are conventional and commonplace in offices, enterprise-wide computer networks, intranets, and the Internet 415.

For purposes of illustration, application programs and other executable program components such as the operating system 405 are illustrated herein as discrete blocks, although it is recognized that such programs and components reside at various times in different storage components of the computing device 401, and are executed by the data processor(s) of the computer. An implementation of imaging software 406 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any method or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. An apparatus for examining an eye, comprising:
    a first light source, wherein the first light source is a laser light source;
    a second light source, wherein the second light source is a Light Emitting Diode (LED) light source;
    a light source selection switch, coupled to the first light source and the second light source, configured to select either the first light source or the second light source to illuminate an eye, wherein the first light source or the second light source becomes a selected light source upon selection;
    a holographic diffuser configured to receive light from the selected light source and to shape the light into a Maxwellian ring based on a diffraction pattern of the holographic diffuser; and
    an imaging lens coupled with a hole mirror, wherein the imaging lens and the hole mirror are configured to receive the Maxwellian ring and to image the Maxwellian ring onto the eye.

2. The apparatus of claim 1, wherein the first light source transmits laser light at 785 nm.

3. The apparatus of claim 1, wherein the second light source transmits red, green, or white light.

4. The apparatus of claim 1, wherein the first light source is selected for imaging blood flow and/or blood vessels having blood flow in the eye.

5. The apparatus of claim 1, wherein the second light source is selected for imaging exudates and other lesions not primarily consisting of blood, that can occur in diabetic retinopathy, hypertension, or macular degeneration.

6. The apparatus of claim 1, wherein the holographic diffuser is generated as a digital hologram, based on a Fourier transform expanded in a Bessel function basis.

7. The apparatus of claim 1, wherein the holographic diffuser is configured to be swappable with a second holographic diffuser in order to adjust a ring diameter and local propagation direction of the light at a pupil of the eye on a per-patient basis.

8. The apparatus of claim 1, further comprising:
    a sensor, configured to receive light reflected from the imaging of the Maxwellian ring and generate an image of the eye based on the reflected light.

9. The apparatus of claim 8, wherein the sensor is a complementary metal oxide semiconductor (CMOS) area sensor.

10. The apparatus of claim 1, further comprising a dichroic mirror that is used to direct light from the first light source or the second light source into the eye.

11. The apparatus of claim 1, further comprising a beamsplitter that is used to direct light from the first light source or the second light source into the eye.

12. A method for examining an eye, comprising:
selecting from a first light source and a second light source, wherein the first light source is a laser light source and the second light source is a Light Emitting Diode (LED) light source, resulting in a selected light source;
transmitting light from the selected light source to a holographic diffuser, wherein the holographic diffuser is configured to shape the light into a Maxwellian ring based on a diffraction pattern of the holographic diffuser;
transmitting the Maxwellian ring from the holographic diffuser to an imaging lens coupled with a hole mirror, wherein the imaging lens and the hole mirror are configured to image the Maxwellian ring based on the diffraction pattern of the holographic diffuser onto the eye; and
imaging the eye with the Maxwellian ring.

13. The method of claim 12, wherein the first light source transmits laser light at 785 nm.

14. The method of claim 12, wherein the second light source transmits red, green, or white light.

15. The method of claim 12, wherein the first light source is selected for imaging blood flow and/or blood vessels having blood flow in the eye.

16. The method of claim 12, wherein the second light source is selected for imaging exudates and other lesions not primarily consisting of blood, that can occur in diabetic retinopathy, hypertension, or macular degeneration.

17. The method of claim 12, further comprising:
generating the holographic diffuser as a digital hologram, based on a Fourier transform expanded in a Bessel function basis.

18. The method of claim 12, further comprising:
swapping the holographic diffuser with a second holographic diffuser in order to adjust a ring diameter and local propagation direction of the light at a pupil of the eye on a per-patient basis.

19. The method of claim 12, further comprising:
receiving light reflected from illuminating the eye with the Maxwellian ring; and
generating an image of the eye based on the reflected light.

20. The method of claim 19, wherein a complementary metal oxide semiconductor (CMOS) area sensor receives the light reflected and generates the image.

21. The method of claim 12, wherein transmitting light from the selected light source to a holographic diffuser comprises transmitting the selected light source through a dichroic mirror that is used to direct light from the selected light source into the eye.

22. The method of claim 12, wherein transmitting light from the selected light source to a holographic diffuser comprises transmitting the selected light source through a beamsplitter that is used to direct light from the selected light source into the eye.

23. A system for examining an eye, comprising:
an apparatus comprising,
a first light source, wherein the first light source is a laser light source,
a second light source, wherein the second light source is a Light Emitting Diode (LED) light source,
a light source selection switch, coupled to the first light source and the second light source, configured to select either the first light source or the second light source to illuminate an eye, wherein the first light source or the second light source becomes a selected light source upon selection,
a holographic diffuser configured to receive light from the selected light source and to shape the light into a Maxwellian ring based on a diffraction pattern of the holographic diffuser,
an imaging lens coupled with a hole mirror, wherein the imaging lens and the hole mirror are configured to receive the Maxwellian ring and to image the Maxwellian ring onto the eye, and
a sensor, configured to receive light reflected from the imaging of the Maxwellian ring and generate an image of the eye based on the reflected light; and
a computing device, coupled to the apparatus, configured to analyze the image of the eye.

24. The system of claim 23, wherein the computing device is configured to analyze the image of the eye to identify blood flow, blood vessels having blood flow, and/or exudates and other lesions not primarily consisting of blood, that can occur in diabetic retinopathy, hypertension, or macular degeneration.

25. The system of claim 23, wherein the apparatus further comprises a dichroic mirror that is used to direct light from the first light source or the second light source into the eye.

26. The system of claim 23, wherein the apparatus further comprises a beamsplitter that is used to direct light from the first light source or the second light source into the eye.

* * * * *

UNITED STATES PATENT AND TRADEMARK OFFICE
CERTIFICATE OF CORRECTION

| | | |
|---|---|---|
| PATENT NO. | : 8,616,702 B2 | Page 1 of 1 |
| APPLICATION NO. | : 13/203168 | |
| DATED | : December 31, 2013 | |
| INVENTOR(S) | : Abramoff | |

It is certified that error appears in the above-identified patent and that said Letters Patent is hereby corrected as shown below:

IN THE SPECIFICATION

Column 1, line 16-19, delete

"This invention was made with government support under Grant No. NIH EY017066-0 which was awarded by the U.S. Department of Health and Human Services. The government has certain rights in the invention."

and insert,

--This invention was made with government support under grant EY017066-0 awarded by the National Institutes of Health. The government has certain rights in this invention.--

Signed and Sealed this
Fifteenth Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,616,702 B2  Page 1 of 1
APPLICATION NO. : 13/203168
DATED : December 31, 2013
INVENTOR(S) : Michael Abrámoff It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 130 days.

Signed and Sealed this
Twenty-second Day of September, 2015

Michelle K. Lee
*Director of the United States Patent and Trademark Office*